United States Patent [19]

Binder et al.

[11] Patent Number: 5,254,574
[45] Date of Patent: Oct. 19, 1993

[54] NEW TETRAZOLE DERIVATIVES, PROCESS FOR THEIR PREPARATION AND THEIR USE

[75] Inventors: Dieter Binder, Wien; Josef Weinberger, Bad Hall; Andreas Koch, Mattersburg, all of Austria

[73] Assignee: Chemisch Pharmazeutische Forschungsgesellschaft m.b.H., Linz, Austria

[21] Appl. No.: 815,199

[22] Filed: Dec. 31, 1991

[30] Foreign Application Priority Data

Jan. 31, 1991 [AT] Austria ............................ A 209/91

[51] Int. Cl.$^5$ .................. C07D 271/06; A61K 31/41
[52] U.S. Cl. .................................... 514/361; 548/131
[58] Field of Search ................... 514/361; 548/131

[56] References Cited

U.S. PATENT DOCUMENTS

| | | | |
|---|---|---|---|
| 4,780,539 | 10/1988 | Watzen | 548/131 |
| 4,952,698 | 8/1990 | Biere | 548/131 |

FOREIGN PATENT DOCUMENTS

| | | |
|---|---|---|
| 253310 | 1/1988 | European Pat. Off. |
| 0291969 | 11/1988 | European Pat. Off. |
| 0323841 | 7/1989 | European Pat. Off. |
| 0324377 | 7/1989 | European Pat. Off. |

OTHER PUBLICATIONS

Wong et al., Journal of Pharmacology and Experimental Therapeutics, pp. 211–217, vol. 255, No. 1, 1990.
Hirotsu et al., J. Chem. Soc. Dalton Trans. (1986), pp. 1609–1611.

*Primary Examiner*—Robert Gerstz
*Attorney, Agent, or Firm*—Wenderoth, Lind & Ponack

[57] ABSTRACT

Tetrazole derivatives of the formula

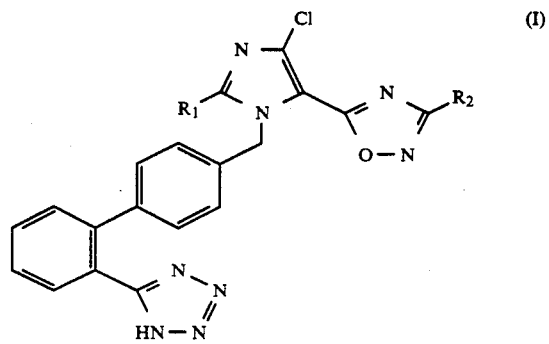

in which $R_1$ denotes a saturated or unsaturated, straight-chain or branched ($C_1$–$C_6$) alkyl radical and $R_2$ denotes methyl or ethyl, and their pharmaceutically usable salts.

6 Claims, 3 Drawing Sheets

NEW TETRAZOLE DERIVATIVES, PROCESS FOR THEIR PREPARATION AND THEIR USE

The invention relates to new therapeutically useful tetrazole derivatives, a process for their preparation and their use.

A large number of compounds which can be used for the treatment of high blood pressure caused by angiotensin II is already known from the literature. A known angiotensin II receptor antagonist, DuP 753 (2-n-butyl-4-chloro-5-hydroxymethyl-1-((2'-(1-H-tetrazol-5-yl)biphenyl-4-yl)methyl)imidazole), is described, for example, in the Journal of Pharmacology and Experimental Therapeutics, P. C. Wong et al. 1990, Volume 255, pages 211–217. However, when used in vivo, DuP 753 is converted into a non-competitive metabolite, EXP 3174 (2-n-butyl-4-chloro-1-((2'-(1H-tetrazol-5-yl)biphenyl-4-yl)methyl)-imidazole-5-carboxylic acid), which is largely responsible for the duration of action of DuP 753. The disadvantage of non-competitive antagonists is, however, that they are bound irreversibly to the receptor and cause changes in the cell structure there.

The object of the present invention was thus to discover purely competitive antagonists which do not form non-competitive metabolites. It has now been unexpectedly possible to achieve this object with the substances according to the invention.

The invention thus relates to new tetrazole derivatives of the formula

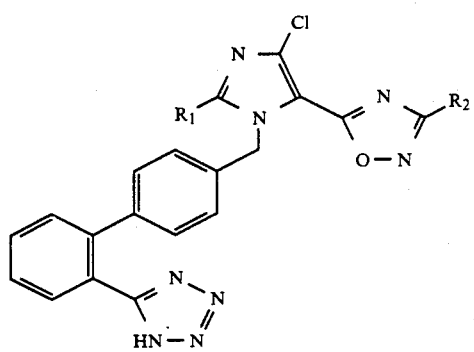

in which $R_1$ denotes a saturated or unsaturated, straight-chain or branched ($C_1$–$C_6$) alkyl radical and $R_2$ denotes methyl or ethyl, and their pharmaceutically usable salts.

In formula I, $R_1$ denotes a saturated or unsaturated, straight-chain or branched ($C_1$–$C_6$) alkyl radical, such as, for example, methyl, ethyl, propyl, i-propyl, butyl, sec-butyl, tert-butyl, hexyl, ethenyl, propenyl or hexenyl. Preferred compounds are those in which $R_1$ denotes butyl, and those in which $R_2$ denotes methyl.

The invention furthermore relates to a process for the preparation of compounds of the formula

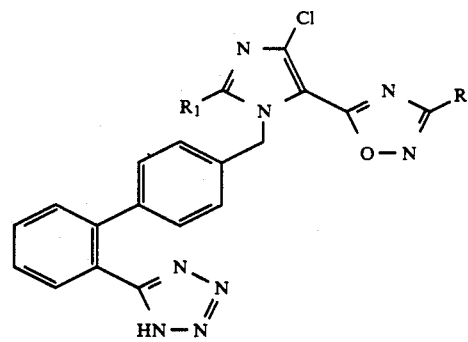

in which $R_1$ denotes a saturated or unsaturated, straight-chain or branched ($C_1$–$C_6$) alkyl radical and $R_2$ denotes methyl or ethyl, and their pharmaceutically usable salts, characterised in that a compound of the formula

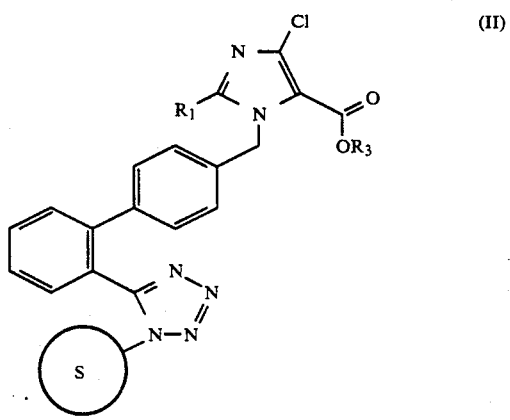

in which $R_1$ has the above meaning, $R_3$ denotes methyl or ethyl and S denotes a protective group, is reacted with a compound of the formula

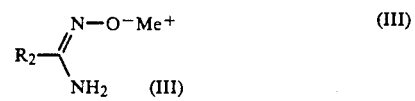

in which $R_2$ denotes methyl or ethyl and Me denotes sodium or potassium, in an organic diluent which is inert under the reaction conditions, under an inert gas atmosphere, to give a compound of the formula

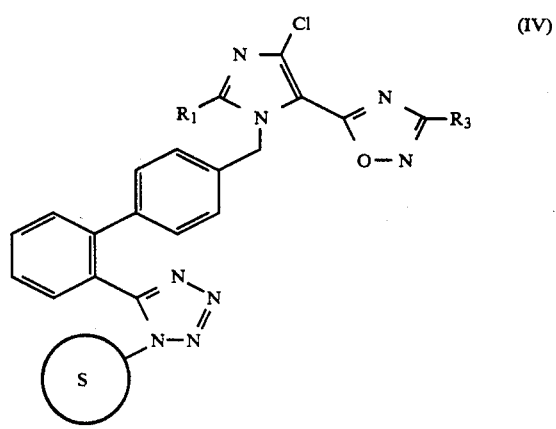

wherein R₁ and R₂ have the above meaning, and the protective group is then removed.

The reaction according to the invention is carried out by reacting a suspension of the compound of the formula III in an anhydrous organic diluent which is inert under the reaction conditions, such as, for example, in an ether, such as, for example, tetrahydrofuran, diethyl ether or dioxane, with a compound of the formula II, dissolved in the same diluent, under an inert gas atmosphere, such as, for example, argon, helium or nitrogen. The reaction temperature is between about $+20°$ and $+40°$ C., preferably between $-10°$ C. and $+20°$ C., and the reaction time depends on the particular reaction partners and the reaction conditions, and is about 2 to 40 hours, preferably 2 to 20 hours. Protective groups which are used are, for example, triphenylmethyl, benzyl, p-nitrobenzyl or 1-ethoxyethyl groups.

The subsequent splitting off of the protective group S from the resulting compounds of the formula IV is carried out, for example, by stirring in a mixture of HBr/glacial acetic acid in chloroform or trifluoroacetic acid in chloroform at room temperature or, preferably, by heating in a lower aliphatic alcohol, such as, for example, methanol or ethanol, depending on the protective group used.

The compounds of the formula II and III are known from the literature (T. Hirotsu et al. J. Chem. Soc. Dalton, 1609, 1986; and D. J. Carini et al. EP 0,324,377, 1989).

The compounds of the formula I can be converted into their pharmaceutically usable salts in the customary manner using inorganic and organic bases. The salt formation can be carried out, for example, by dissolving the compounds of the formula I mentioned in a suitable agent, for example water, a lower aliphatic alcohol, an ether, such as tetrahydrofuran, dioxane or diethyl ether, dimethylformamide or dimethyl sulfoxide, adding an equivalent amount of the desired base, ensuring thorough mixing and, when the salt formation has ended, evaporating off the solvent. If appropriate, the salts can be recrystallized after isolation.

Pharmaceutically usable salts are, for example, metal salts, in particular alkali metal or alkaline earth metal salts, such as salts of sodium, potassium, magnesium or calcium. Other pharmaceutically usable salts are, for example, ammonium salts which crystallize readily. The latter are derived from ammonia or organic amines, for example from mono-, di- or trialkyl-, -cycloalkyl- or -hydroxyalkyl-amines, alkylenediamines or hydroxyalkyl-, arylalkyl- or alkylammonium bases, for example methylamine, diethylamine, triethylamine, dicyclohexylamine, triethanolamine, ethylenediamine, tris(hydroxymethyl)aminomethane, benzyltrimethylammonium hydroxide and the like.

The new compounds of the formula I and their salts have an oral action and suppress the vasoconstrictive and hypertensive action of angiotensin II. In animal models, the compounds exhibit an outstanding antihypertensive action.

Thus, for example (FIG. 1), the dose/effect curve of angiotensin II is shifted to the right as a function of the dose and competitively. In comparison experiments with DuP 753, it is found that although this substance also acts competitively in experiments in vitro (FIG. 2), in experiments in vivo (FIG. 3) conversion into an active non-competitive metabolite is detectable in the longer duration of action compared with the substances according to the invention. Experiments by Wong et al., 1990, JPET, Volume 255, pages 211–217, have shown that this active metabolite EXP 3174, a non-competitive irreversible angiotensin II receptor antagonist, is responsible for the long duration of action. In contrast, the substances according to the invention are bound reversibly to the receptor, so that this is not changed or destroyed. This reversible binding manifests itself in the shorter duration of action, which also demonstrates that these substances act without an active noncompetitive metabolite.

On the basis of these pharmacological properties, the new compounds can be used as medicines for the treatment of high blood pressure and other cardiovascular diseases by themselves or as a mixture with other active substances, in the form of a customary pharmaceutical formulation.

The invention furthermore relates to medicaments which are used, for example, in the form of pharmaceutical preparations which contain the compounds of the formula I according to the invention or their salts as a mixture with one or more pharmaceutical organic or inorganic excipients suitable for enteral or parenteral administration, for example water, gelatin, gum arabic, lactose, starch, magnesium stearate, talc, vegetable oils, polyalkylene glycols, vaseline or the like.

The pharmaceutical preparations can be in solid form, for example as tablets, film-coated tablets, sugar-coated tablets, suppositories, capsules or microcapsules, or in liquid form, for example as solutions, injection solutions, suspensions or emulsions, or in compositions with a delayed release of the active compound. If appropriate they are sterilized and/or contain auxiliaries, such as preservatives, stabilizers, emulsifiers, salts for modifying the osmotic pressure or buffers.

In particular, pharmaceutical preparations can contain the compounds according to the invention in combination with other therapeutically useful substances. The compounds according to the invention can be formulated with these, together with the abovementioned auxiliaries and/or excipients, to give combination preparations.

A suitable dose for administration of the new compounds is about 4–200 mg/kg per day, and the preferred daily dose/patient is about 60–200 mg, although other doses are also possible, depending on the condition of the patient to be treated. The new compounds can be administered in several doses and orally.

The new compounds can be present in the pharmaceutical compositions according to the invention in an amount of about 4–200 mg per tablet, preferably about 20–50 mg per tablet, the remainder being a pharmaceutically acceptable filler.

EXAMPLE 1

5-(4'-(2-Butyl-4-chloro-5-(3-methyl-1,2,4-oxadiazol-5-yl)-1-imidazolylmethyl)biphenyl-2-yl)-1-triphenylmethyl-1H-tetrazole 0.09 g (0.0038 mol) of sodium hydride is added to a solution of 0.28 g (0.0038 mol) of N-hydroxyethaneimidamide in 20 ml of absolute tetrahydrofuran, and this suspension is heated at 60° C. over a molecular sieve under a nitrogen atmosphere for one hour. The mixture is cooled to 0° C. and a solution of 2.20 g (0.0032 mol) of methyl 1-((2,-(N-triphenylmethyl-tetrazol-5-yl)-biphenyl-4-yl)-methyl)- 2-butyl-4-chloro-1H-imidazole-5-carboxylate in 45 ml of absolute tetrahydrofuran is rapidly added dropwise. The suspension is heated to room temperature and stirred for 18 hours.

The reaction mixture is filtered and the filtrate is evaporated in vacuo. The residue is partitioned between 10 ml of water and 10 ml of ethyl acetate, the phases are separated and the aqueous phase is extracted with 3×20 ml of ethyl acetate. The combined organic phases are dried over sodium sulfate and filtered and the solvent is stripped off. The product is purified by column chromatography. (Silica gel 60; 30 g; mobile phase: toluene-:ethyl acetate =10:1). The product is made to crystallize by digestion in ether.

Yield: 1.00 g of colorless crystals (43% of theory)
Melting point: 175°-177° C. (acetone)
Thin layer chromatography: solvent: toluene : ethyl acetate= 10 : 1; $R_f$=0.4
Elemental microanalysis:
$C_{43}H_{37}N_8ClO$ Molecular weight=717.28 C H N
calculated 72.01 5.20 15.62
found 71.80 5.37 15.68

$^1$H-NMR (CDCl$_3$)
delta (ppm): 7.93-7.87 (m; 1H; Bz—H$_3$'); 7.63-7.47 (m; 2H; Bz—H$_5$', —H$_6$'); 7.41-7.26 (m; 1H; Bz—H$_4$'); 7.39-7.28 (m; 10H; Bz—H); 7.11; 7.07; 6.78; 6.72 (A$_2$B$_2$; 4H; Bz—H$_2$, —H$_6$and Bz—H$_3$,—H$_5$,); 6.99-6.89 (m; 6H; Bz—H); 5.67 (s; 2H; Im—CH$_2$—Bz); 2.53 (t; 2H; Bu$_1$—CH$_2$); 2.35 (s;3H —CH$_3$); 1.63 (m; 2H; Bu-$_2$—CH$_2$); 1.22 (m; 2H; Bu$_3$—CH$_2$); 0.84 (t; 3H; Bu—CH$_3$)

$^{13}$C-NMR (CDCl$_3$)
delta (ppm): 166.68; 163.92; 153.06; 141.21; 140.94; 134.16; 130.72; 130.21; 129.98; 129.83; 128.26; 127.61; 126.22; 125.53; 113.83; 82.87; 48.49; 29.29; 26.94; 22.31; 13.70; 11.51

5-(4'-(2-Butyl-4-chloro-5-(3-methyl-1,2,4-oxadiazol-5-yl)-1-imidazolylmethyl)biphenyl-2-yl)-1H-tetrazole.

0.40 g (0.0006 mol) of 5-(4'-(2-butyl-4-chloro-5-(3-methyl-1,2,4-oxadiazol-5-yl)-1-imidazolyl-methyl)-biphenyl-2-yl)-1-triphenylmethyl-1H-tetrazole is suspended in 12 ml of methanol and heated at the boiling point for two hours. The solvent is stripped off, the residue is digested with 3 ml of boiling diethyl ether under the influence of heat and the resulting crystals are filtered off. The crude product is recrystallized from ethyl acetate/active charcoal.

Yield: 0.10 g of colorless crystals (35% of theory)
Melting point: 178°-180° C. (ethyl acetate)
Thin layer chromatography: solvent: benzene: dioxane: acetic acid=8:1:1; $R_f$=0.6
Elemental microanalysis: $C_{24}H_{23}N_8ClO$ Molecular weight=474.96 C H N calculated 60.69 4.88 23.59 found 60.51 4.94 23.29 $^1$H-NMR (CDCl$_3$)
delta (ppm): 7.93-7.87 (m; 1H; Bz-H$_3$'); 7.63-7.47 (m; 2H; Bz-H$_5$',—H$_6$'); 7.41-7.26 (m; 1H; Bz-H$_4$'); 7.11; 7.07; 6.92; 6.87 (A$_2$B$_2$; 4H; Bz—H$_2$, H$_6$ and Bz—H$_3$, —H$_5$,) 5.67 (s; 2H; Im—CH$_2$—Bz); 2.53 (t; 2H; Bu-$_1$—CH$_2$); 2.35 (s; 3H; —CH$_3$); 1.63 (m; 2H; Bu$_2$—CH$_2$); 1.22 (m; 2H; Bu$_3$—CH$_2$); 0.84 (t; 3H; Bu—CH$_3$)

$^{13}$C-NMR (CDCl$_3$)
delta (ppm): 166.94; 166.36; 153.01; 140.58; 139.30; 135.51; 135.16; 131.38; 130.79; 130.66; 129.60; 128.42; 126.25; 122.89; 113.54; 48.59; 29.56; 26.74; 22.27; 13.66; 11.54

EXAMPLE 2

Angiotensin II - receptor-antagonistic effects of the substance (subst. 1) in comparison to DuP 753
a) isolated rat aorta:
Cumulative dose-response curves to angiotensin II (10$^{-10}$-10$^{-7}$mol/l) were performed isometrically with and without pretreatment with subst. 1 or DuP 753 (10−8, 10$^{-7}$, 10$^{-6}$ mol/1, each) and results were expressed as percentage of maximum contraction obtained by addition of 10$^{-5}$ mol/1 noradrenaline.

EP$_{50}$-values and pA$_2$-values were determined arithmetically.

| Angiotensin II | +10$^{-8}$ mol/l Subst. 1 | +10$^{-7}$ mol/l Subst. 1 | +10$^{-6}$ mol/l Subst. 1 |
|---|---|---|---|
| n = 8 | n = 8 | n = 8 | n = 8 |
| ED50 = 7,9.10$^{-10}$ mol/l | ED50 = 7,9.10$^{-9}$ mol/l | ED50 = 1,9.10$^{-8}$ mol/l | ED50 = 1,7.10$^{-7}$ mol/l |

Figure 1:
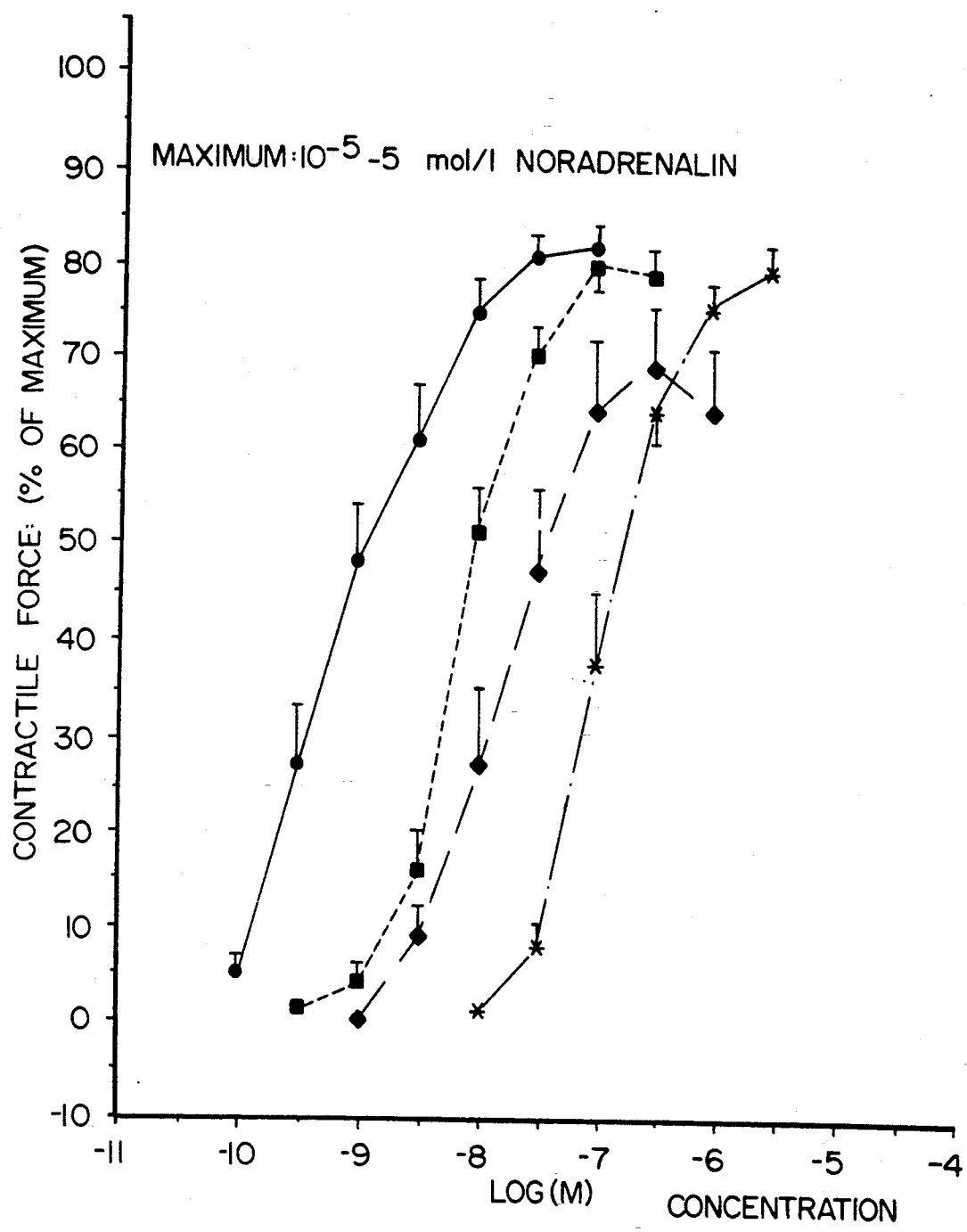
FIG. 1 Isolated rat aorta contractile force of subst. 1
Figure 2:
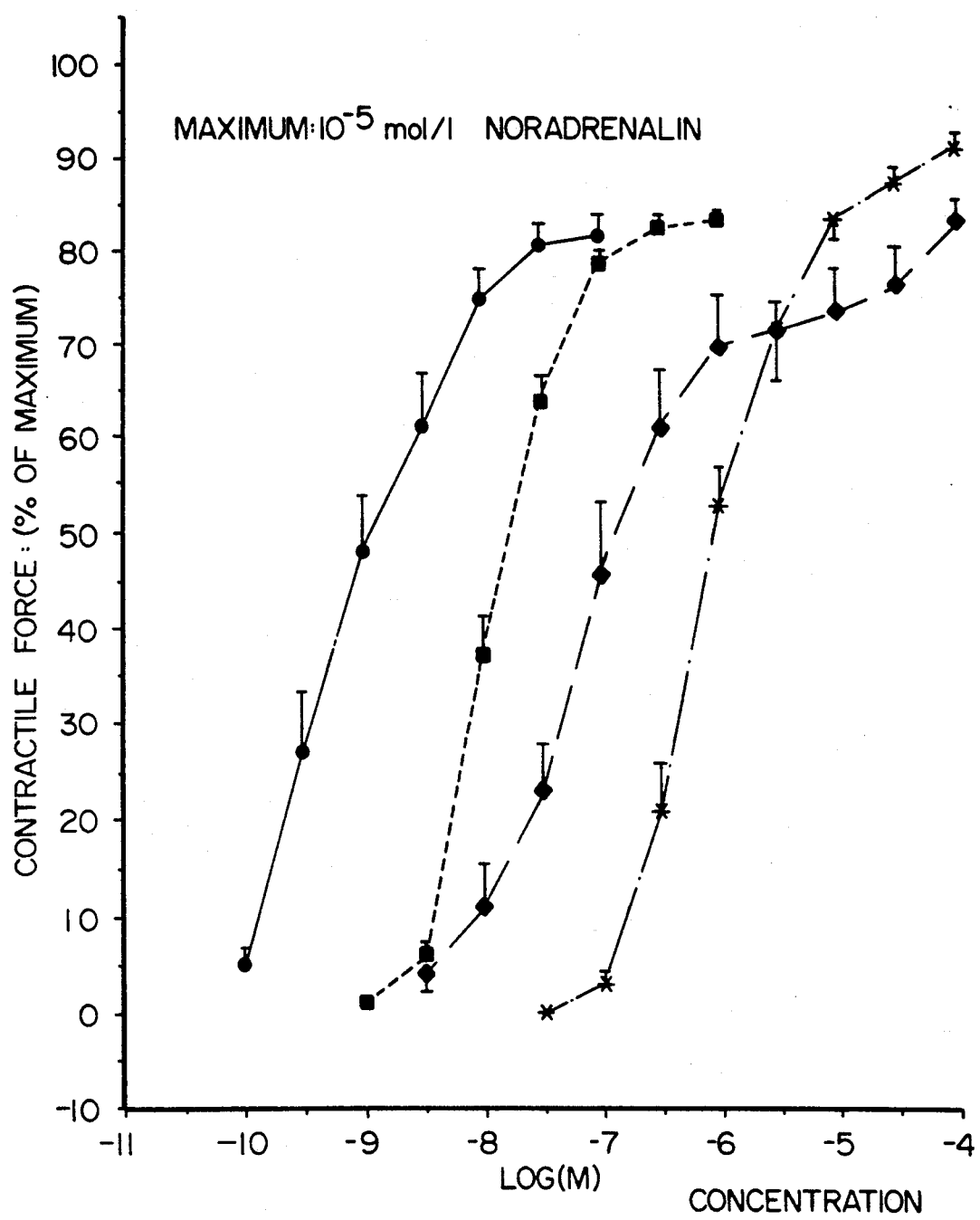

FIG. 2 Isolated rat aorta contractile force of DuP 753

| Angiotensin II | +10$^{-8}$ mol/l DuP 753 | +10$^{-7}$ mol/l DuP 753 | +10$^{-6}$ mol/l DuP 753 |
|---|---|---|---|
| n = 8 | n = 8 | n = 8 | n = 8 |
| ED50 = 7,9.10$^{-10}$ mol/l | ED50 = 1,6.10$^{-8}$ mol/l | ED50 = 1,4.10$^{-7}$ mol/l | ED50 = 1,0.10$^{-6}$ mol/l | b) anaesthetized normotensive rat: Angiotension II (1 /ug/kg i.v.) was given before as well as in 15 minutes intervals after intraduodenal administration of the drugs.

Figure 3:
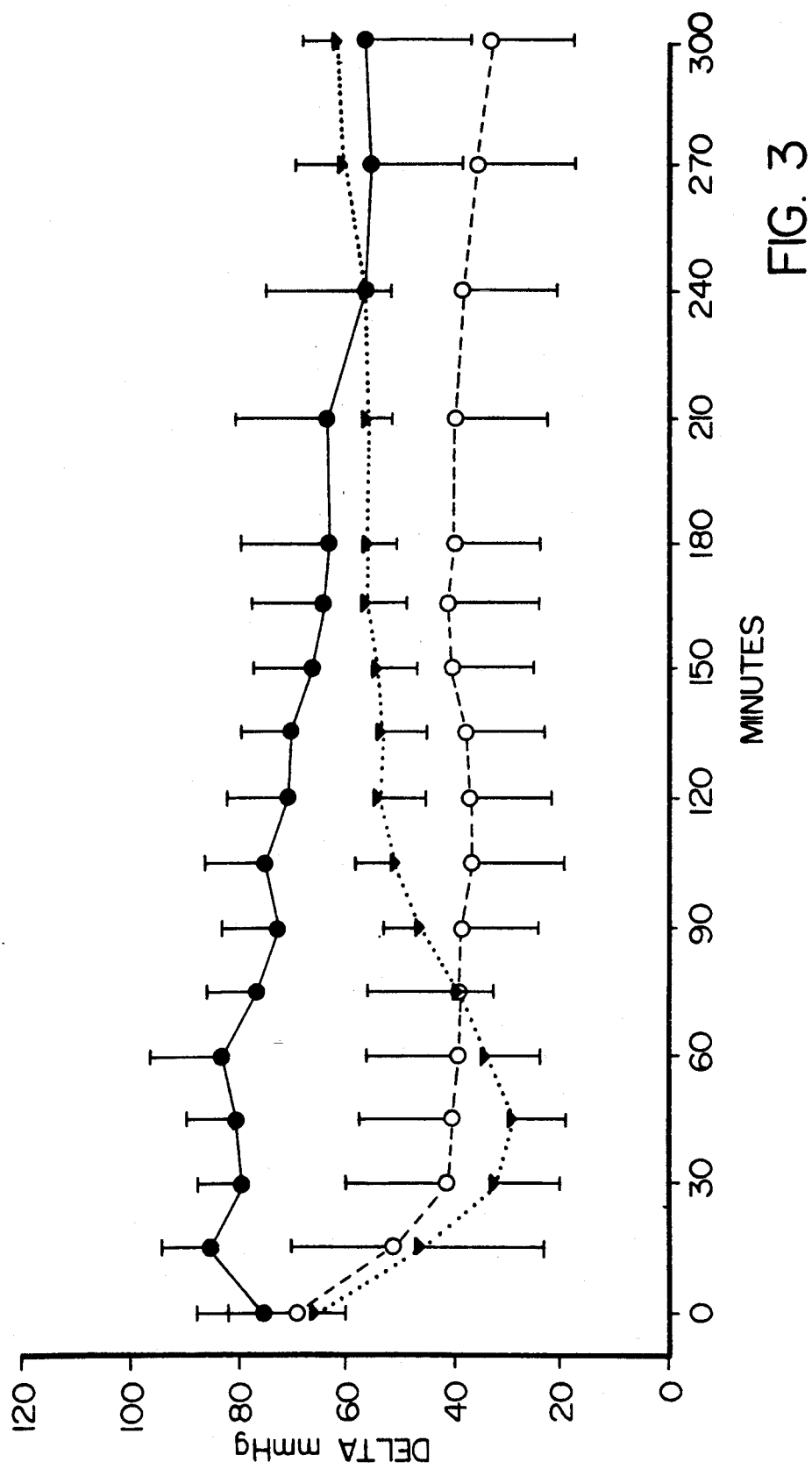

FIG. 3 The effects of DuP 753 and Subst. 1 on angiotension II induced increases in mean arterial bloodpessure in normotensive anaesthetized rats (n=4)

What we claim is
1. New tetrazole derivatives of the formula

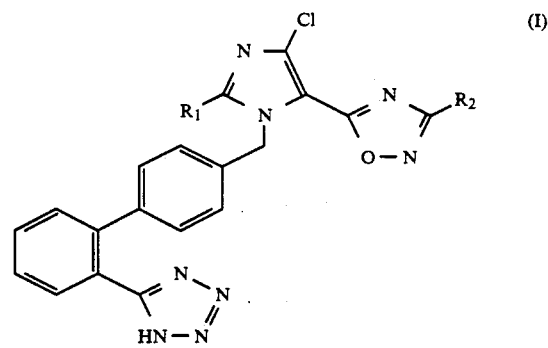

in which R$_1$ denotes a saturated or unsaturated, straight-chain or branched (C$_1$-C$_6$) alkyl radical and R$_2$ denotes methyl or ethyl, and their pharmaceutically usable salts.

2. Compounds of the formula I defined in claim 1, wherein R$_1$ denotes butyl.

3. 5-(4'-(2-Butyl-4-chloro-5-(3-methyl-1,2,4-oxadiazol-5yl)-1-imidazolylmethyl)biphenyl-2-yl)-1H-tetrazole.

4. Pharmaceutical preparations containing compounds of the formula I according to claim 1 and salts thereof, in combination with customary pharmaceutical auxiliaries and/or excipients.

5. Pharmaceutical preparations containing compounds of the formula I according to claim 1 and salts thereof, in combination with other therapeutically useful active compounds and customary pharmaceutical auxiliaries and/or excipients.

6. A method of inhibiting angiotensin II in a patient in need of such inhibition, which comprises administering to the patient a therapeutically effective amount of a compound of the formula I according to claim 1 or salt thereof.

* * * * *

UNITED STATES PATENT AND TRADEMARK OFFICE
CERTIFICATE OF CORRECTION

PATENT NO. : 5,254,574
DATED : October 19, 1993
INVENTOR(S) : Dieter BINDER, Josef WEINBERGER and Andreas KOCH It is certified that error appears in the above-indentified patent and that said Letters Patent is hereby corrected as shown below:

Column 3, line 11, change "+20°" to -- -20°--.

Column 6, below the first occurrence of "mol/l" at line 17, insert -- —●—●—●— --;

below the second occurrence of "mol/l" at line 17, insert -- —■—■—■— --;

below the third occurrence of "mol/l" at line 17, insert -- —◆—◆—◆— --;

below the fourth occurrence of "mol/l" at line 17, insert -- —✹—✹—✹— --;

below the first occurrence of "mol/l" at line 28, insert -- —●—●—●— --;

below the second occurrence of "mol/l" at line 28, insert -- —■—■—■— --;

UNITED STATES PATENT AND TRADEMARK OFFICE
CERTIFICATE OF CORRECTION

PATENT NO. : 5,254,574
DATED : October 19, 1993
INVENTOR(S) : Dieter BINDER, Josef WEINBERGER and Andreas KOCH It is certified that error appears in the above-indentified patent and that said Letters Patent is hereby corrected as shown below:

column 6, below the third occurrence of "mol/l" at line 28, insert -- ◆ ◆ ◆ -- --;

below the fourth occurrence of "mol/l" at line 28, insert -- ✳ ✳ ✳ -- --; and below line 37, insert -- ●   Control Methocel 0.5 % i. d.

○   DuP 753 10 mg/kg i. d.

▼   Subst. 1 30 mg/kg i. d. --.

Signed and Sealed this

Tenth Day of May, 1994

BRUCE LEHMAN

*Attest:*

*Attesting Officer*   *Commissioner of Patents and Trademarks*